(12) United States Patent
Sowards et al.

(10) Patent No.: US 12,733,899 B2
(45) Date of Patent: Sep. 15, 2026

(54) NON-UNIFORM ULTRASOUND IMAGE MODIFICATION OF TARGETED SUB-REGIONS

(71) Applicant: Bard Access Systems, Inc., Salt Lake City, UT (US)

(72) Inventors: Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 460 days.

(21) Appl. No.: 17/957,562

(22) Filed: Sep. 30, 2022

(65) Prior Publication Data

US 2023/0107629 A1 Apr. 6, 2023

Related U.S. Application Data

(60) Provisional application No. 63/252,048, filed on Oct. 4, 2021.

(51) Int. Cl.
*A61B 8/08* (2006.01)
*A61B 8/00* (2006.01)

(52) U.S. Cl.
CPC .......... *A61B 8/0841* (2013.01); *A61B 8/4416* (2013.01); *A61B 8/4433* (2013.01); *A61B 8/465* (2013.01)

(58) Field of Classification Search
None
See application file for complete search history.

(56) References Cited

U.S. PATENT DOCUMENTS 3,697,917 A 10/1972 Orth et al.
5,148,809 A 9/1992 Biegeleisen-Knight et al.
(Continued)

FOREIGN PATENT DOCUMENTS

CN 102871645 A 1/2013
CN 105107067 B 5/2018
(Continued)

OTHER PUBLICATIONS

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).
(Continued)

*Primary Examiner* — Christopher Koharski
*Assistant Examiner* — Farouk A Bruce
(74) *Attorney, Agent, or Firm* — Rutan & Tucker LLP

(57) ABSTRACT

Embodiments disclosed herein are directed to a non-uniform, targeted ultrasound image modification system. The system can image a target area using ultrasound and can determine one or more target locations within the target area. Further the system can determine a location and orientation of a medical device to overlay a trajectory onto the target area. A user can further modify the one or more target locations as needed. The user can then modify an image parameter for the target area, and can further modify an image parameter for one or more target locations independently of the target area. This allows a user to modify the image of the target location to suit the position, tissue structure, or a procedure taking place there without affecting the image quality of the rest of the target area, or other target locations.

19 Claims, 5 Drawing Sheets

(56) References Cited

U.S. PATENT DOCUMENTS 5,181,513 A 1/1993 Touboul et al.
5,325,293 A 6/1994 Dorne
5,349,865 A 9/1994 Kavli et al.
5,441,052 A 8/1995 Miyajima
5,549,554 A 8/1996 Miraki
5,573,529 A 11/1996 Haak et al.
5,758,650 A 6/1998 Miller et al.
5,775,322 A 7/1998 Silverstein et al.
5,879,297 A 3/1999 Haynor et al.
5,897,503 A 4/1999 Lyon et al.
5,908,387 A 6/1999 LeFree et al.
5,967,984 A 10/1999 Chu et al.
5,970,119 A 10/1999 Hofmann
6,004,270 A 12/1999 Urbano et al.
6,019,724 A 2/2000 Gronningsaeter et al.
6,068,599 A 5/2000 Saito et al.
6,074,367 A 6/2000 Hubbell
6,129,668 A 10/2000 Haynor et al.
6,132,379 A 10/2000 Patacsil et al.
6,216,028 B1 4/2001 Haynor et al.
6,233,476 B1 5/2001 Strommer et al.
6,245,018 B1 6/2001 Lee
6,263,230 B1 7/2001 Haynor et al.
6,375,615 B1 4/2002 Flaherty et al.
6,436,043 B2 8/2002 Bonnefous
6,498,942 B1 12/2002 Esenaliev et al.
6,503,205 B2 1/2003 Manor et al.
6,508,769 B2 1/2003 Bonnefous
6,511,458 B2 1/2003 Milo et al.
6,524,249 B2 2/2003 Moehring et al.
6,543,642 B1 4/2003 Milliorn
6,554,771 B1 4/2003 Buil et al.
6,592,520 B1 7/2003 Peszynski et al.
6,592,565 B2 7/2003 Twardowski
6,601,705 B2 8/2003 Molina et al.
6,612,992 B1 9/2003 Hossack et al.
6,613,002 B1 9/2003 Clark et al.
6,623,431 B1 9/2003 Sakuma et al.
6,641,538 B2 11/2003 Nakaya et al.
6,647,135 B2 11/2003 Bonnefous
6,687,386 B1 2/2004 Ito et al.
6,733,458 B1 5/2004 Steins et al.
6,749,569 B1 6/2004 Pellegretti
6,754,608 B2 6/2004 Svanerudh et al.
6,755,789 B2 6/2004 Stringer et al.
6,840,379 B2 1/2005 Franks-Farah et al.
6,857,196 B2 2/2005 Dalrymple
6,979,294 B1 12/2005 Selzer et al.
7,074,187 B2 7/2006 Selzer et al.
7,244,234 B2 7/2007 Ridley et al.
7,359,554 B2 4/2008 Klingensmith et al.
7,534,209 B2 5/2009 Abend et al.
7,599,730 B2 10/2009 Hunter et al.
7,637,870 B2 12/2009 Flaherty et al.
7,681,579 B2 3/2010 Schwartz
7,691,061 B2 4/2010 Hirota
7,699,779 B2 4/2010 Sasaki et al.
7,720,520 B2 5/2010 Willis
7,727,153 B2 6/2010 Fritz et al.
7,734,326 B2 6/2010 Pedain et al.
7,831,449 B2 11/2010 Ying et al.
7,905,837 B2 3/2011 Suzuki
7,925,327 B2 4/2011 Weese
7,927,278 B2 4/2011 Selzer et al.
8,014,848 B2 9/2011 Birkenbach et al.
8,038,619 B2 10/2011 Steinbacher
8,060,181 B2 11/2011 Rodriguez Ponce et al.
8,075,488 B2 12/2011 Burton
8,090,427 B2 1/2012 Eck et al.
8,105,239 B2 1/2012 Specht
8,172,754 B2 5/2012 Watanabe et al.
8,175,368 B2 5/2012 Sathyanarayana
8,200,313 B1 6/2012 Rambod et al.
8,211,023 B2 7/2012 Swan et al.
8,228,347 B2 7/2012 Beasley et al.
8,298,147 B2 10/2012 Huennekens et al.
8,303,505 B2 11/2012 Webler et al.
8,323,202 B2 12/2012 Roschak et al.
8,328,727 B2 12/2012 Miele et al.
8,336,536 B1 12/2012 Wood-Putnam et al.
8,388,541 B2 3/2013 Messerly et al.
8,409,103 B2 4/2013 Grunwald et al.
8,449,465 B2 5/2013 Nair et al.
8,553,954 B2 10/2013 Saikia
8,556,815 B2 10/2013 Pelissier et al.
8,585,600 B2 11/2013 Liu et al.
8,622,913 B2 1/2014 Dentinger et al.
8,706,457 B2 4/2014 Hart et al.
8,727,988 B2 5/2014 Flaherty et al.
8,734,357 B2 5/2014 Taylor
8,744,211 B2 6/2014 Owen
8,754,865 B2 6/2014 Merritt et al.
8,764,663 B2 7/2014 Smok et al.
8,781,194 B2 7/2014 Malek et al.
8,781,555 B2 7/2014 Burnside et al.
8,790,263 B2 7/2014 Randall et al.
8,849,382 B2 9/2014 Cox et al.
8,939,908 B2 1/2015 Suzuki et al.
8,961,420 B2 2/2015 Zhang
9,022,940 B2 5/2015 Meier
9,087,147 B1 7/2015 Fonte
9,138,290 B2 9/2015 Hadjicostis
9,199,082 B1 12/2015 Yared et al.
9,204,858 B2 12/2015 Pelissier et al.
9,220,477 B2 12/2015 Urabe et al.
9,295,447 B2 3/2016 Shah
9,320,493 B2 4/2016 Visveshwara
9,357,980 B2 6/2016 Toji et al.
9,364,171 B2 6/2016 Harris et al.
9,427,207 B2 8/2016 Sheldon et al.
9,445,780 B2 9/2016 Hossack et al.
9,456,766 B2 10/2016 Cox et al.
9,456,804 B2 10/2016 Tamada
9,468,413 B2 10/2016 Hall et al.
9,492,097 B2 11/2016 Wilkes et al.
9,521,961 B2 12/2016 Silverstein et al.
9,554,716 B2 1/2017 Burnside et al.
9,582,876 B2 2/2017 Specht
9,610,061 B2 4/2017 Ebbini et al.
9,636,031 B2 5/2017 Cox
9,649,037 B2 5/2017 Lowe et al.
9,649,048 B2 5/2017 Cox et al.
9,702,969 B2 7/2017 Hope Simpson et al.
9,715,757 B2 7/2017 Ng et al.
9,717,415 B2 8/2017 Cohen et al.
9,731,066 B2 8/2017 Liu et al.
9,814,433 B2 11/2017 Benishti et al.
9,814,531 B2 11/2017 Yagi et al.
9,861,337 B2 1/2018 Patwardhan et al.
9,895,138 B2 2/2018 Sasaki
9,913,605 B2 3/2018 Harris et al.
9,949,720 B2 4/2018 Southard et al.
10,043,272 B2 8/2018 Forzoni et al.
10,449,330 B2 10/2019 Newman et al.
10,524,691 B2 1/2020 Newman et al.
10,751,509 B2 8/2020 Misener
11,564,861 B1 1/2023 Gaines
11,844,656 B2 12/2023 Urabe et al.
11,900,593 B2 2/2024 Dhatt et al.
12,082,976 B2 9/2024 Urabe et al.
2002/0038088 A1 3/2002 Imran et al.
2003/0047126 A1 3/2003 Tomaschko
2003/0106825 A1 6/2003 Molina et al.
2003/0109910 A1 6/2003 Lachenbruch et al.
2003/0120154 A1 6/2003 Sauer et al.
2003/0125629 A1 7/2003 Ustuner
2003/0135115 A1 7/2003 Burdette et al.
2003/0149366 A1 8/2003 Stringer et al.
2003/0167030 A1 9/2003 Weitzel et al.
2003/0216648 A1 11/2003 Lizzi et al.
2004/0015080 A1 1/2004 Kelly et al.
2004/0055925 A1 3/2004 Franks-Farah et al.
2004/0197267 A1 10/2004 Black et al.
2005/0000975 A1 1/2005 Carco et al.

(56) References Cited

U.S. PATENT DOCUMENTS

2005/0049504 A1 3/2005 Lo et al.
2005/0075597 A1 4/2005 Vournakis et al.
2005/0165299 A1 7/2005 Kressy et al.
2005/0251030 A1 11/2005 Azar et al.
2005/0267365 A1 12/2005 Sokulin et al.
2006/0004290 A1 1/2006 Smith et al.
2006/0013523 A1 1/2006 Childlers et al.
2006/0015039 A1 1/2006 Cassidy et al.
2006/0020204 A1 1/2006 Serra et al.
2006/0047617 A1 3/2006 Bacioiu et al.
2006/0079781 A1 4/2006 Germond-Rouet et al.
2006/0184029 A1 8/2006 Haim et al.
2006/0210130 A1 9/2006 Germond-Rouet et al.
2006/0241463 A1 10/2006 Shau et al.
2007/0043341 A1 2/2007 Anderson et al.
2007/0049822 A1 3/2007 Bunce et al.
2007/0073155 A1 3/2007 Park et al.
2007/0167738 A1 7/2007 Timinger et al.
2007/0199848 A1 8/2007 Ellswood et al.
2007/0239005 A1* 10/2007 Ogasawara ............ A61B 8/467 600/437
2007/0239120 A1 10/2007 Brock et al.
2007/0249911 A1 10/2007 Simon
2007/0287886 A1 12/2007 Saadat
2008/0021322 A1 1/2008 Stone et al.
2008/0033293 A1 2/2008 Beasley et al.
2008/0033759 A1 2/2008 Finlay
2008/0051657 A1 2/2008 Rold
2008/0108930 A1 5/2008 Weitzel et al.
2008/0125651 A1 5/2008 Watanabe et al.
2008/0146915 A1 6/2008 McMorrow
2008/0177186 A1 7/2008 Slater et al.
2008/0221425 A1 9/2008 Olson et al.
2008/0269605 A1 10/2008 Nakaya
2008/0294037 A1 11/2008 Richter
2008/0300491 A1 12/2008 Bonde et al.
2009/0012399 A1 1/2009 Sunagawa et al.
2009/0012401 A1 1/2009 Steinbacher
2009/0074280 A1 3/2009 Lu et al.
2009/0105594 A1 4/2009 Reynolds et al.
2009/0118612 A1 5/2009 Grunwald et al.
2009/0124903 A1 5/2009 Osaka
2009/0137887 A1 5/2009 Shariati et al.
2009/0137907 A1 5/2009 Takimoto et al.
2009/0143672 A1 6/2009 Harms et al.
2009/0143684 A1 6/2009 Cermak et al.
2009/0156926 A1 6/2009 Messerly et al.
2009/0171205 A1 7/2009 Kharin et al.
2009/0281413 A1 11/2009 Boyden et al.
2009/0306509 A1 12/2009 Pedersen et al.
2010/0010348 A1 1/2010 Halmann
2010/0168576 A1 7/2010 Poland et al.
2010/0211026 A2 8/2010 Sheetz et al.
2010/0249598 A1 9/2010 Smith et al.
2010/0286515 A1 11/2010 Gravenstein et al.
2010/0298705 A1 11/2010 Pelissier et al.
2010/0312121 A1 12/2010 Guan
2010/0324423 A1 12/2010 El-Aklouk et al.
2011/0002518 A1 1/2011 Ziv-Ari et al.
2011/0026796 A1 2/2011 Hyun et al.
2011/0071404 A1 3/2011 Schmitt et al.
2011/0074244 A1 3/2011 Osawa
2011/0087107 A1 4/2011 Lindekugel et al.
2011/0137173 A1 6/2011 Lowe et al.
2011/0166451 A1 7/2011 Blaivas et al.
2011/0282188 A1 11/2011 Burnside et al.
2011/0295108 A1 12/2011 Cox et al.
2011/0313293 A1 12/2011 Lindekugel et al.
2012/0136242 A1 5/2012 Qi et al.
2012/0136256 A1 5/2012 Nozaki et al.
2012/0143029 A1 6/2012 Silverstein et al.
2012/0165679 A1 6/2012 Orome et al.
2012/0179038 A1 7/2012 Meurer et al.
2012/0179042 A1 7/2012 Fukumoto et al.
2012/0179044 A1 7/2012 Chiang et al.
2012/0197132 A1 8/2012 O'Connor
2012/0220865 A1 8/2012 Brown et al.
2012/0277576 A1 11/2012 Lui
2013/0041250 A1 2/2013 Pelissier et al.
2013/0102889 A1 4/2013 Southard et al.
2013/0131499 A1 5/2013 Chan et al.
2013/0131502 A1 5/2013 Blaivas et al.
2013/0144166 A1 6/2013 Specht et al.
2013/0150724 A1 6/2013 Blaivas et al.
2013/0188832 A1 7/2013 Ma et al.
2013/0197367 A1 8/2013 Smok et al.
2013/0218024 A1 8/2013 Boctor et al.
2013/0323700 A1 12/2013 Samosky et al.
2013/0338503 A1 12/2013 Cohen et al.
2013/0338508 A1 12/2013 Nakamura et al.
2013/0345566 A1 12/2013 Weitzel et al.
2014/0005530 A1 1/2014 Liu et al.
2014/0031694 A1 1/2014 Solek
2014/0066779 A1 3/2014 Nakanishi
2014/0073976 A1 3/2014 Fonte et al.
2014/0100440 A1 4/2014 Cheline et al.
2014/0114194 A1 4/2014 Kanayama et al.
2014/0170620 A1 6/2014 Savitsky et al.
2014/0180098 A1 6/2014 Flaherty et al.
2014/0180116 A1 6/2014 Lindekugel et al.
2014/0188133 A1 7/2014 Misener
2014/0188440 A1 7/2014 Donhowe et al.
2014/0276048 A1 9/2014 Kiley et al.
2014/0276059 A1 9/2014 Sheehan
2014/0276069 A1 9/2014 Amble et al.
2014/0276081 A1 9/2014 Tegels
2014/0276085 A1 9/2014 Miller
2014/0276690 A1 9/2014 Grace
2014/0296694 A1 10/2014 Jaworski
2014/0343431 A1 11/2014 Vajinepalli et al.
2014/0357994 A1 12/2014 Jin et al.
2015/0005738 A1 1/2015 Blacker
2015/0011887 A1 1/2015 Ahn et al.
2015/0065916 A1 3/2015 Maguire et al.
2015/0073279 A1 3/2015 Cai et al.
2015/0080740 A1 3/2015 Hao et al.
2015/0112200 A1 4/2015 Oberg et al.
2015/0141821 A1 5/2015 Yoshikawa et al.
2015/0190111 A1 7/2015 Fry
2015/0209003 A1 7/2015 Halmann et al.
2015/0209113 A1 7/2015 Burkholz et al.
2015/0209510 A1 7/2015 Burkholz et al.
2015/0209526 A1 7/2015 Matsubara et al.
2015/0245820 A1 9/2015 Tamada
2015/0257735 A1 9/2015 Ball et al.
2015/0272448 A1 10/2015 Fonte et al.
2015/0282890 A1 10/2015 Cohen et al.
2015/0294497 A1 10/2015 Ng et al.
2015/0297097 A1 10/2015 Matsubara et al.
2015/0342572 A1* 12/2015 Tahmasebi Maraghoosh ............ A61B 34/20 600/424
2015/0359520 A1 12/2015 Shan et al.
2015/0359991 A1 12/2015 Dunbar et al.
2016/0000367 A1 1/2016 Lyon
2016/0000399 A1 1/2016 Halmann et al.
2016/0026894 A1 1/2016 Nagase
2016/0029995 A1 2/2016 Navratil et al.
2016/0038119 A1 2/2016 Desjardins
2016/0081674 A1 3/2016 Bagwan et al.
2016/0113517 A1 4/2016 Lee et al.
2016/0113699 A1 4/2016 Sverdlik et al.
2016/0120607 A1 5/2016 Sorotzkin et al.
2016/0125639 A1 5/2016 Park et al.
2016/0157831 A1 6/2016 Kang et al.
2016/0166232 A1 6/2016 Merritt
2016/0202053 A1 7/2016 Walker et al.
2016/0211045 A1 7/2016 Jeon et al.
2016/0213398 A1 7/2016 Liu
2016/0220124 A1 8/2016 Grady et al.
2016/0259992 A1 9/2016 Knodt et al.
2016/0278869 A1 9/2016 Grunwald
2016/0287214 A1* 10/2016 Ralovich ................ A61B 8/469
2016/0296208 A1 10/2016 Sethuraman et al.

(56) References Cited

U.S. PATENT DOCUMENTS

2016/0374644 A1 12/2016 Mauldin, Jr. et al.
2017/0014105 A1 1/2017 Chono
2017/0020561 A1 1/2017 Cox et al.
2017/0079548 A1 3/2017 Silverstein et al.
2017/0086785 A1 3/2017 Bjaerum
2017/0090571 A1 3/2017 Bjaerum et al.
2017/0103534 A1 4/2017 Park et al.
2017/0143312 A1 5/2017 Hedlund et al.
2017/0157339 A1 6/2017 Li et al.
2017/0164923 A1 6/2017 Matsumoto
2017/0172666 A1 6/2017 Govari et al.
2017/0215842 A1 8/2017 Ryu et al.
2017/0231553 A1 8/2017 Igarashi et al.
2017/0252004 A1 9/2017 Broad et al.
2017/0258522 A1 9/2017 Goshgarian et al.
2017/0259013 A1 9/2017 Boyden et al.
2017/0262982 A1 9/2017 Pagoulatos et al.
2017/0328751 A1 11/2017 Lemke
2017/0367678 A1 12/2017 Sirtori et al.
2018/0015256 A1 1/2018 Southard et al.
2018/0028110 A1 2/2018 Goldman et al.
2018/0116723 A1 5/2018 Hettrick et al.
2018/0125450 A1 5/2018 Blackbourne et al.
2018/0161502 A1 6/2018 Nanan et al.
2018/0199914 A1 7/2018 Ramachandran et al.
2018/0214119 A1 8/2018 Mehrmohammadi et al.
2018/0228465 A1 8/2018 Southard et al.
2018/0235649 A1 8/2018 Elkadi
2018/0235709 A1 8/2018 Donhowe et al.
2018/0289927 A1 10/2018 Messerly
2018/0296185 A1 10/2018 Cox et al.
2018/0310955 A1 11/2018 Lindekugel et al.
2018/0333135 A1 11/2018 Kim et al.
2018/0344293 A1 12/2018 Raju et al.
2019/0029636 A1 1/2019 Lee et al.
2019/0060001 A1 2/2019 Kohli et al.
2019/0060014 A1 2/2019 Hazelton et al.
2019/0090855 A1 3/2019 Kobayashi et al.
2019/0125210 A1 5/2019 Govari et al.
2019/0200951 A1 7/2019 Meier
2019/0239848 A1 8/2019 Bedi et al.
2019/0239850 A1 8/2019 Dalvin et al.
2019/0307419 A1 10/2019 Durfee
2019/0307515 A1 10/2019 Naito et al.
2019/0307516 A1 10/2019 Schotzko et al.
2019/0365347 A1 12/2019 Abe
2019/0365348 A1 12/2019 Toume et al.
2019/0365354 A1 12/2019 Du
2019/0380676 A1 12/2019 Swan et al.
2020/0027210 A1 1/2020 Haemel et al.
2020/0069929 A1 3/2020 Mason et al.
2020/0085381 A1 3/2020 Weine et al.
2020/0107596 A1 4/2020 Caruso et al.
2020/0113540 A1 4/2020 Gijsbers et al.
2020/0163654 A1 5/2020 Satir et al.
2020/0200900 A1 6/2020 Asami et al.
2020/0229795 A1 7/2020 Tadross et al.
2020/0230391 A1 7/2020 Burkholz et al.
2020/0237403 A1* 7/2020 Southard ................ A61B 8/461
2020/0238403 A1 7/2020 Ahn et al.
2020/0281563 A1 9/2020 Muller et al.
2020/0359990 A1 11/2020 Poland et al.
2020/0390416 A1 12/2020 Swan et al.
2021/0045716 A1 2/2021 Shiran et al.
2021/0059639 A1 3/2021 Howell
2021/0077058 A1 3/2021 Mashood et al.
2021/0093383 A1 4/2021 Wang et al.
2021/0137492 A1 5/2021 Imai
2021/0146167 A1 5/2021 Barthe et al.
2021/0161510 A1 6/2021 Sasaki et al.
2021/0186467 A1 6/2021 Urabe et al.
2021/0212658 A1 7/2021 McGrath et al.
2021/0212668 A1 7/2021 Li et al.
2021/0267569 A1 9/2021 Yamamoto
2021/0267570 A1 9/2021 Ulman et al.
2021/0295048 A1 9/2021 Buras et al.
2021/0315538 A1 10/2021 Brandl et al.
2021/0373602 A1 12/2021 Min
2021/0378627 A1 12/2021 Yarmush et al.
2022/0019313 A1 1/2022 He et al.
2022/0022969 A1 1/2022 Misener
2022/0039777 A1 2/2022 Durfee
2022/0039829 A1 2/2022 Zijlstra et al.
2022/0071593 A1 3/2022 Tran
2022/0096053 A1 3/2022 Sethuraman et al.
2022/0096797 A1 3/2022 Prince
2022/0101980 A1 3/2022 Rothenberg et al.
2022/0104791 A1 4/2022 Matsumoto
2022/0104886 A1 4/2022 Blanchard et al.
2022/0117582 A1 4/2022 McLaughlin et al.
2022/0160434 A1 5/2022 Messerly et al.
2022/0168050 A1 6/2022 Sowards et al.
2022/0172354 A1 6/2022 Misener et al.
2022/0225963 A1 7/2022 Sutton et al.
2022/0233346 A1 7/2022 McElya
2022/0296303 A1 9/2022 McLeod et al.
2022/0304652 A1 9/2022 Peterson et al.
2022/0330922 A1 10/2022 Sowards et al.
2022/0334251 A1 10/2022 Sowards et al.
2022/0338833 A1 10/2022 Dhatt et al.
2022/0361840 A1 11/2022 Matsumoto et al.
2022/0406460 A1 12/2022 Golan et al.
2023/0044620 A1 2/2023 Shochat et al.
2023/0048327 A1 2/2023 Lampe et al.
2023/0113291 A1 4/2023 de Wild et al.
2023/0132148 A1 4/2023 Sowards et al.
2023/0135562 A1 5/2023 Misener et al.
2023/0135757 A1 5/2023 Bauer et al.
2023/0138970 A1 5/2023 Sowards et al.
2023/0148872 A1 5/2023 Sowards et al.
2023/0201539 A1 6/2023 Howell
2023/0277153 A1 9/2023 Sowards et al.
2023/0277154 A1 9/2023 Sowards et al.
2023/0293143 A1 9/2023 Sowards et al.
2023/0298757 A1 9/2023 Golan et al.
2023/0338010 A1 10/2023 Sturm
2023/0371928 A1* 11/2023 Rajguru ................ A61B 8/465
2023/0381472 A1 11/2023 Chisena et al.
2023/0397900 A1 12/2023 Prince
2024/0065673 A1 2/2024 Sowards et al.
2024/0197403 A1 6/2024 Mino et al.
2024/0307024 A1 9/2024 Sowards et al.
2025/0017559 A1 1/2025 Denny et al.
2025/0057501 A1 2/2025 Prince
2025/0104238 A1 3/2025 Misener et al.
2025/0177060 A1 6/2025 Messerly et al.
2025/0186026 A1 6/2025 Tran
2025/0251511 A1 8/2025 Sowards et al.
2025/0352167 A1 11/2025 Sowards et al.
2026/0123906 A1 5/2026 Sowards et al.

FOREIGN PATENT DOCUMENTS

EP 0933063 A1 8/1999
EP 1504713 A1 2/2005
EP 1591074 B1 5/2008
EP 2823766 A1 1/2015
EP 3181083 A1 6/2017
EP 3870059 9/2021
JP 2000271136 A 10/2000
JP 2007222291 A 9/2007
JP 2014150928 A 8/2014
JP 2018175547 A 11/2018
KR 20180070878 A 6/2018
KR 102176196 B1 11/2020
WO 2004082749 A2 9/2004
WO 2007115174 A2 10/2007
WO 2010029521 A2 3/2010
WO 2010076808 A1 7/2010
WO 2013059714 A1 4/2013
WO 2014/115150 A1 7/2014
WO 2015/017270 A1 2/2015
WO 2016/081023 A1 5/2016
WO 2017096487 A1 6/2017

(56) References Cited

FOREIGN PATENT DOCUMENTS

| | | | |
|---|---|---|---|
| WO | 2017214428 | A1 | 12/2017 |
| WO | 2018/026878 | A1 | 2/2018 |
| WO | 2018134726 | A1 | 7/2018 |
| WO | 2018138343 | A1 | 8/2018 |
| WO | 2019/232451 | A1 | 12/2019 |
| WO | 2020/002620 | A1 | 1/2020 |
| WO | 2020/016018 | A1 | 1/2020 |
| WO | 2019/232454 | A9 | 2/2020 |
| WO | 2020/044769 | A1 | 3/2020 |
| WO | 2020067897 | A1 | 4/2020 |
| WO | 2020083660 | A1 | 4/2020 |
| WO | 2020/186198 | A1 | 9/2020 |
| WO | 2021123905 | A2 | 6/2021 |
| WO | 2021198226 | A1 | 10/2021 |
| WO | 2022/072727 | A2 | 4/2022 |
| WO | 2022/081904 | A1 | 4/2022 |
| WO | 2022069208 | A1 | 4/2022 |
| WO | 2022/119853 | A1 | 6/2022 |
| WO | 2022115479 | A1 | 6/2022 |
| WO | 2022119856 | A1 | 6/2022 |
| WO | 2022/221703 | A1 | 10/2022 |
| WO | 2022/221714 | A1 | 10/2022 |
| WO | 2023059512 | A1 | 4/2023 |
| WO | 2023076268 | A1 | 5/2023 |
| WO | 2023081220 | A1 | 5/2023 |
| WO | 2023081223 | A1 | 5/2023 |
| WO | 2023091424 | A1 | 5/2023 |
| WO | 2023167866 | A1 | 9/2023 |
| WO | 2023177718 | A1 | 9/2023 |
| WO | 2024044277 | A1 | 2/2024 |
| WO | 2024180503 | A1 | 9/2024 |
| WO | 2025/015198 | A1 | 1/2025 |

OTHER PUBLICATIONS

Pagoulatos, N. et al. "New spatial localizer based on fiber optics with applications in 3D ultrasound imaging" Proceeding of Spie, vol. 3976 (Apr. 18, 2000; Apr. 18, 2000).

PCT/US2021/049294 filed Sep. 7, 2021 International Search Report and Written Opinion dated Dec. 8, 2021.

PCT/US2021/049712 filed Sep. 9, 2021 International Search Report and Written Opinion dated Dec. 14, 2021.

PCT/US2021/060622 filed Nov. 23, 2021 International Search Report and Written Opinion dated Mar. 3, 2022.

PCT/US2021/061267 filed Nov. 30, 2021 International Search Report and Written Opinion dated Mar. 9, 2022.

PCT/US2021/061276 filed Nov. 30, 2021 International Search Report and Written Opinion dated Mar. 9, 2022.

PCT/US2022/025082 filed Apr. 15, 2022 International Search Report and Written Opinion dated Jul. 11, 2022.

PCT/US2022/025097 filed Apr. 15, 2022 International Search Report and Written Opinion dated Jul. 8, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.

U.S. Appl. No. 15/650,474, filed Jul. 14, 2017 Final Office Action dated Jun. 2, 2020.

U.S. Appl. No. 15/650,474, filed Jul. 14, 2017 Non-Final Office Action dated Dec. 16, 2019.

U.S. Appl. No. 15/650,474, filed Jul. 14, 2017 Notice of Allowance dated Dec. 11, 2020.

U.S. Appl. No. 15/650,474, filed Jul. 14, 2017 Notice of Allowance dated Mar. 1, 2021.

U.S. Appl. No. 17/020,476, filed Sep. 14, 2020 Advisory Action dated Aug. 19, 2022.

U.S. Appl. No. 17/020,476, filed Sep. 14, 2020 Final Office Action dated Jun. 9, 2022.

U.S. Appl. No. 17/020,476, filed Sep. 14, 2020 Non-Final Office Action dated Feb. 9, 2022.

U.S. Appl. No. 17/020,476, filed Sep. 14, 2020 Non-Final Office Action dated Sep. 23, 2022.

U.S. Appl. No. 17/471,015, filed Sep. 9, 2021 Non-Final Office Action dated Aug. 16, 2022.

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

PCT/US2022/048716 filed Nov. 2, 2022 International Search Report and Written Opinion dated Feb. 24, 2023.

PCT/US2022/048722 filed Nov. 2, 2022 International Search Report and Written Opinion dated Feb. 24, 2023.

PCT/US2022047727 filed Oct. 25, 2022 International Search Report and Written Opinion dated Jan. 25, 2023.

U.S. Appl. No. 17/020,476, filed Sep. 14, 2020 Final Office Action dated Jan. 5, 2023.

U.S. Appl. No. 17/471,015, filed Sep. 9, 2021 Non-Final Office Action dated Mar. 30, 2023.

U.S. Appl. No. 17/534,099, filed Nov. 23, 2021 Non-Final Office Action dated Mar. 31, 2023.

U.S. Appl. No. 17/538,911, filed Nov. 30, 2021 Non-Final Office Action dated Mar. 2, 2023.

PCT/US2022/049983 filed Nov. 15, 2022 International Search Report and Written Opinion dated Mar. 29, 2023.

PCT/US2023/014143 filed Feb. 28, 2023 International Search Report and Written Opinion dated Jun. 12, 2023.

PCT/US2023/015266 filed Mar. 15, 2023 International Search Report and Written Opinion dated May 25, 2023.

Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.

U.S. Appl. No. 17/020,476, filed Sep. 14, 2020 Notice of Allowance dated Apr. 28, 2022.

U.S. Appl. No. 17/468,318, filed Sep. 7, 2021 Non-Final Office Action dated Apr. 12, 2023.

U.S. Appl. No. 17/684,180, filed Mar. 1, 2022 Restriction Requirement dated May 19, 2023.

EP 20866520.8 filed Apr. 5, 2022 Extended European Search Report dated Aug. 22, 2023.

U.S. Appl. No. 17/468,318, filed Sep. 7, 2021 Final Office Action dated Sep. 8, 2023.

U.S. Appl. No. 17/538,911, filed Nov. 30, 2021 Final Office Action dated Sep. 13, 2023.

U.S. Appl. No. 17/684,180, filed Mar. 1, 2022 Non-Final Office Action dated Jul. 28, 2023.

U.S. Appl. No. 17/722,151, filed Apr. 15, 2022 Non-Final Office Action dated Sep. 7, 2023.

PCT/US2022/025097 filed Apr. 15, 2021 International Preliminary Report on Patentability dated Oct. 26, 2023.

PCT/US2023/030970 filed Aug. 23, 2023 International Search Report and Written Opinion dated Oct. 30, 2023.

U.S. Appl. No. 17/468,318, filed Sep. 7, 2021 Advisory Action dated Nov. 6, 2023.

U.S. Appl. No. 17/471,015, filed Sep. 9, 2021 Final Office Action dated Oct. 12, 2023.

U.S. Appl. No. 17/534,099, filed Nov. 23, 2021 Advisory Action dated Dec. 8, 2023.

U.S. Appl. No. 17/534,099, filed Nov. 23, 2021 Final Office Action dated Sep. 29, 2023.

U.S. Appl. No. 17/538,911, filed Nov. 30, 2021 Advisory Action dated Nov. 22, 2023.

U.S. Appl. No. 17/722,151, filed Apr. 15, 2022 Advisory Action dated Jan. 2, 2024.

U.S. Appl. No. 17/722,151, filed Apr. 15, 2022 Final Office Action dated Nov. 6, 2023.

U.S. Appl. No. 17/894,460, filed Aug. 24, 2022 Non-Final Office Action dated Nov. 6, 2023.

M. Ikhsan, K. K. Tan, AS. Putra, C. F. Kong, et. al., "Automatic identification of blood vessel cross-section for central venous catheter placement using a cascading classifier," 39th Annual Interna-

(56) References Cited

OTHER PUBLICATIONS tional Conference of the IEEE Engineering in Medicine and Biology Society (EMBC).pp. 1489-1492 (Year: 2017).
U.S. Appl. No. 17/468,318, filed Sep. 7, 2021 Notice of Allowance dated Jan. 18, 2024.
U.S. Appl. No. 17/471,015, filed Sep. 9, 2021 Advisory Action dated Feb. 2, 2024.
U.S. Appl. No. 17/471,015, filed Sep. 9, 2021 Non-Final Office Action dated Mar. 28, 2024.
U.S. Appl. No. 17/534,099, filed Nov. 23, 2021 Non-Final Office Action dated Mar. 14, 2024.
U.S. Appl. No. 17/538,911, filed Nov. 30, 2021 Notice of Allowance dated Mar. 14, 2024.
U.S. Appl. No. 17/538,943, filed Nov. 30, 2021 Non-Final Office Action dated Jan. 30, 2024.
U.S. Appl. No. 17/684,180, filed Mar. 1, 2022 Advisory Action dated Apr. 4, 2024.
U.S. Appl. No. 17/684,180, filed Mar. 1, 2022 Final Office Action dated Jan. 18, 2024.
U.S. Appl. No. 17/722,111, filed Apr. 15, 2022 Non-Final Office Action dated Dec. 22, 2023.
U.S. Appl. No. 17/722,151, filed Apr. 15, 2022 Non-Final Office Action dated Mar. 25, 2024.
U.S. Appl. No. 17/894,460, filed Aug. 24, 2022 Advisory Action dated Apr. 4, 2024.
U.S. Appl. No. 17/894,460, filed Aug. 24, 2022 Final Office Action dated Jan. 31, 2024.
U.S. Appl. No. 18/238,281, filed Aug. 25, 2023 Non-Final Office Action dated Mar. 22, 2024.
PCT/US2022/045372 filed Sep. 30, 2022 International Search Report and Written Opinion dated Jan. 14, 2023.
U.S. Appl. No. 17/538,943, filed Nov. 30, 2021 Notice of Allowance dated Aug. 14, 2024.
U.S. Appl. No. 17/684,180, filed Mar. 1, 2022 Non-Final Office Action dated May 8, 2024.
U.S. Appl. No. 17/722,111, filed Apr. 15, 2022 Final Office Action dated Jul. 12, 2024.
U.S. Appl. No. 17/979,564, filed Nov. 2, 2022 Non-Final Office Action dated Jun. 5, 2024.
U.S. Appl. No. 17/979,601, filed Nov. 2, 2022 Non-Final Office Action dated Aug. 20, 2024.
U.S. Appl. No. 18/238,281, filed Aug. 25, 2023 Notice of Allowance dated Jul. 16, 2024.
U.S. Appl. No. 17/684,180, filed Mar. 1, 2022 Advisory Action dated Dec. 27, 2024.
U.S. Appl. No. 17/684,180, filed Mar. 1, 2022 Non-Final Office Action dated Jan. 17, 2025.
U.S. Appl. No. 17/722,111, filed Apr. 15, 2022 Notice of Allowance dated Dec. 18, 2024.
U.S. Appl. No. 17/722,151, filed Apr. 15, 2022 Advisory Action dated Dec. 27, 2024.
U.S. Appl. No. 17/894,460, filed Aug. 24, 2022 Final Office Action dated Dec. 31, 2024.
U.S. Appl. No. 17/973,171, filed Oct. 25, 2022 Non-Final Office Action dated Dec. 6, 2024.
U.S. Appl. No. 17/979,564, filed Nov. 2, 2022 Advisory Action dated Jan. 17, 2025.
U.S. Appl. No. 17/979,601, filed Nov. 2, 2022 Advisory Action dated Feb. 11, 2025.
U.S. Appl. No. 17/979,601, filed Nov. 2, 2022 Final Office Action dated Dec. 5, 2024.
U.S. Appl. No. 17/987,698, filed Nov. 15, 2022 Advisory Action dated Feb. 21, 2025.
U.S. Appl. No. 17/987,698, filed Nov. 15, 2022 Final Office Action dated Dec. 13, 2024.
U.S. Appl. No. 18/121,802, filed Mar. 15, 2023 Non-Final Office Action dated Dec. 16, 2024.
U.S. Appl. No. 18/674,601, filed May 24, 2024 Non-Final Office Action dated Jan. 7, 2025.
U.S. Appl. No. 17/684,180, filed Mar. 1, 2022 Final Office Action dated May 29, 2025.
U.S. Appl. No. 17/722,151, filed April 15, 2022 Non-Final Office Action dated Mar. 21, 2025.
U.S. Appl. No. 17/894,460, filed Aug. 24, 2022 Advisory Action dated Mar. 13, 2025.
U.S. Appl. No. 17/973,171, filed Oct. 25, 2022 Final Office Action dated Apr. 3, 2025.
U.S. Appl. No. 17/979,601, filed Nov. 2, 2022 Notice of Allowance dated Mar. 27, 2025.
U.S. Appl. No. 17/987,698, filed Nov. 15, 2022 Non-Final Office Action dated May 23, 2025.
U.S. Appl. No. 18/113,003, filed Feb. 22, 2023 Final Office Action dated Apr. 29, 2025.
U.S. Appl. No. 18/221,318, filed Jul. 12, 2023 Restriction Requirement dated Mar. 28, 2025.
U.S. Appl. No. 18/674,601, filed May 24, 2024 Notice of Allowance dated Mar. 26, 2025.
Chen et al.,3D near infrared and ultrasound imaging of peripheral blood vessels for real-time localization and needle guidance. InMedical Image Computing and Computer-Assisted Intervention—MICCAI 2016 (pp. 388-396) (Year: 2016).
Konica Minolta, "Vascular NAVI" product website. https://www.konicaminolta.com/global-en/healthcare/technology/ultrasound/vascularnavi/index.html. Last accessed Jun. 2025.
U.S. Appl. No. 17/684,180, filed Mar. 1, 2022 Advisory Action dated Aug. 22, 2025.
U.S. Appl. No. 17/722,151, filed Apr. 15, 2022 Final Office Action dated Jul. 11, 2025.
U.S. Appl. No. 17/973,171, filed Oct. 25, 2022 Advisory Action dated Jun. 30, 2025.
U.S. Appl. No. 17/979,564, filed Nov. 2, 2022 Examiner's Answer dated May 30, 2025.
U.S. Appl. No. 18/113,003, filed Feb. 22, 2023 Advisory Action dated Jul. 2, 2025.
U.S. Appl. No. 18/113,003, filed Feb. 22, 2023 Notice of Allowance dated Aug. 15, 2025.
U.S. Appl. No. 18/121,802, filed Mar. 15, 2023 Notice of Allowance dated Jun. 5, 2025.
U.S. Appl. No. 18/221,318, filed Jul. 12, 2023 Non-Final Office Action dated Jun. 23, 2025.
U.S. Appl. No. 17/722,151, filed Apr. 15, 2022 Non-Final Office Action dated Dec. 23, 2025.
U.S. Appl. No. 17/894,460, filed Aug. 24, 2022 Non-Final Office Action dated Jan. 14, 2026.
U.S. Appl. No. 17/973,171, filed Oct. 25, 2022 Examiner's Answer dated Jan. 28, 2026.
U.S. Appl. No. 17/979,564, filed Nov. 2, 2022 Board Decision dated Mar. 4, 2026.
U.S. Appl. No. 17/987,698, filed Nov. 15, 2022 Non-Final Office Action dated Mar. 16, 2026.
U.S. Appl. No. 19/042,983, filed Jan. 31, 2025 Notice of Allowance dated Feb. 24, 2026.
U.S. Appl. No. 17/684,180, filed Mar. 1, 2022 Notice of Allowance dated Sep. 30, 2025.
U.S. Appl. No. 17/722,151, filed Apr. 15, 2022 Advisory Action dated Oct. 16, 2025.
U.S. Appl. No. 17/894,460, filed Aug. 24, 2022 Examiner's Answer dated Oct. 2, 2025.
U.S. Appl. No. 17/987,698, filed Nov. 15, 2022 Advisory Action dated Nov. 21, 2025.
U.S. Appl. No. 17/987,698, filed Nov. 15, 2022 Final Office Action dated Sep. 12, 2025.
U.S. Appl. No. 18/221,318, filed Jul. 12, 2023 Final Office Action dated Oct. 14, 2025.
U.S. Appl. No. 18/936,351, filed Nov. 4, 2024 Non-Final Office Action dated Nov. 10, 2025.
PCT/US2024/037647 filed Jul. 11, 2024 International Search Report and Written Opinion dated Oct. 16, 2024.
Thermographic venous blood flow characterization with external cooling stimulation (Year: 2018).
U.S. Appl. No. 17/471,015, filed Sep. 9, 2021 Notice of Allowance dated Oct. 29, 2024.

(56) References Cited

OTHER PUBLICATIONS

U.S. Appl. No. 17/534,099, filed Nov. 23, 2021 Notice of Allowance dated Sep. 18, 2024.
U.S. Appl. No. 17/684,180, filed Mar. 1, 2022 Final Office Action dated Sep. 23, 2024.
U.S. Appl. No. 17/722,111, filed Apr. 15, 2022 Advisory Action dated Oct. 23, 2024.
U.S. Appl. No. 17/722,151, filed Apr. 15, 2022 Final Office Action dated Sep. 20, 2024.
U.S. Appl. No. 17/894,460, filed Aug. 24, 2022 Non-Final Office Action dated Sep. 25, 2024.
U.S. Appl. No. 17/979,564, filed Nov. 2, 2022 Final Office Action dated Oct. 18, 2024.
U.S. Appl. No. 17/987,698, filed Nov. 15, 2022 Non-Final Office Action dated Sep. 20, 2024.
U.S. Appl. No. 18/113,003, filed Feb. 22, 2023 Non-Final Office Action dated Nov. 27, 2024.
Sonka, Momodou L., T. Campbell Arnold, and Ivan A. Kuznetsov. "Machine learning in point of care ultrasound." POCUS journal 7. Kidney (2022): 78. (Year: 2022).
US 17/722, 151 filed Apr. 15, 2022 Notice of Allowance dated Jun. 9, 2026.
U.S. Appl. No. 17/979,564, filed Nov. 2, 2022 Notice of Allowance dated May 29, 2026.
U.S. Appl. No. 18/221,318, filed Jul. 12, 2023 Non-Final Office Action dated May 6, 2026.
U.S. Appl. No. 18/936,351, filed Nov. 4, 2024 Notice of Allowance dated Jun. 10, 2026.
U.S. Appl. No. 19/058,331, filed Feb. 20, 2025 Notice of Allowance dated Apr. 20, 2026.
U.S. Appl. No. 19/251,382, filed Jun. 26, 2025 Restriction Requirement dated May 18, 2026.

* cited by examiner 130
132
80
120
128
150
80
160A
80
160B
82
102
128
104
100

NON-UNIFORM ULTRASOUND IMAGE MODIFICATION OF TARGETED SUB-REGIONS

PRIORITY

This application claims the benefit of priority to U.S. Provisional Application No. 63/252,048, filed Oct. 4, 2021, which is incorporated by reference in its entirety into this application.

SUMMARY

Briefly summarized, embodiments disclosed herein are directed to a non-uniform, targeted ultrasound image modification system and associated methods thereof. The system can determine one or more targeted sub-regions, or "target locations," within an imaged target area, including vessel detection and/or image plane intercept identification and can modify one or more imaging parameters to suit each of the one or more target regions.

When imaging a subcutaneous target area using traditional ultrasound imaging techniques, a clinician can modify various imaging parameters to optimize the image depending on the depth, type of target location within the target area, specific tissue being imaged, or the like. These image parameters can include, but not limited to, the image focus, contrast, gain, and/or other image transforms. However, modifying the image parameters can only be applied broadly across the entire image and do not improve visibility of all mediums or regions of interest within the image, especially where there are multiple target locations or procedures being performed.

Disclosed herein is an imaging system configured to select one or more target locations within an imaged target area and modify one or more image parameters for a first target location independently of the target area. As such, specific target locations can be optimized for visualization without negatively impacting the visibility of the surrounding area that require different optimal visualization criteria.

Disclosed herein is a subcutaneous imaging system including, a probe configured to emit an ultrasonic signal and receive a reflected ultrasonic signal, a console communicatively coupled to the probe and including a display, the console configured to, i) receive information from the probe and display an image of a subcutaneous target area, ii) determine a target location within the target area, iii) modify a first image parameter of the target area to a first value, and iv) modify a second image parameter of the target location to a second value different from the first value.

In some embodiments, the console is further configured to determine one or both of a location and an orientation of a medical device, relative to the probe, and overlay an icon on the target area to indicate one or more of the location, the orientation, or a trajectory of the medical device relative to the target area. In some embodiments, the medical device includes a magnetic field having a magnetic field strength, and wherein the probe is configured to detect the magnetic field strength of the medical device to determine one or both of a location and an orientation of a medical device. In some embodiments, the medical device includes one of a needle, stylet, guidewire, trocar, or a catheter.

In some embodiments, the console is further configured to determine the target location within the target area using one or more of artificial intelligence, machine learning, neural networks, or Doppler ultrasonography. In some embodiments, the console is further configured to receive an input from a user to determine the target location within the target area. In some embodiments, one or both of the first image parameter and the second image parameter includes one of an image focus, image contrast, image gain, or an image transform. In some embodiments, one of the first value or the second value includes one of a quantitative value or qualitative value. In some embodiments, the target location can include one or more of a vessel, a tissue structure, a point of interception, or a region of the target area.

Also disclosed is a method of imaging system a subcutaneous target area including, displaying an image of the target area using a medical imaging system, determining a target location within the target area, modifying a first image parameter of the target area to a first value, and modifying a second image parameter of the target location to a second value different from the first value.

In some embodiments, the medical imaging system includes an ultrasound imaging system having a console and a probe. In some embodiments, the method further includes displaying an icon on the image of the target area to indicate one or more of a location, orientation, or trajectory of a medical device relative to the target area. In some embodiments, the method further includes detecting a magnetic field strength of the medical device to determine one or both of the location and the orientation of a medical device. In some embodiments, the medical device includes one of a needle, stylet, guidewire, trocar, or a catheter.

In some embodiments, determining the target location within the target area further includes using one or more of artificial intelligence, machine learning, neural networks, or Doppler ultrasonography. In some embodiments, the console is further configured to receive an input from a user to determine the target location within the target area. In some embodiments, one or both of the first image parameter and the second image parameter includes one or more of an image focus, image contrast, image gain, and an image transform. In some embodiments, one of the first value or the second value includes one of a quantitative value or qualitative value. In some embodiments, the target location can include one or more of a vessel, a tissue structure, a point of interception, or a region of the target area.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
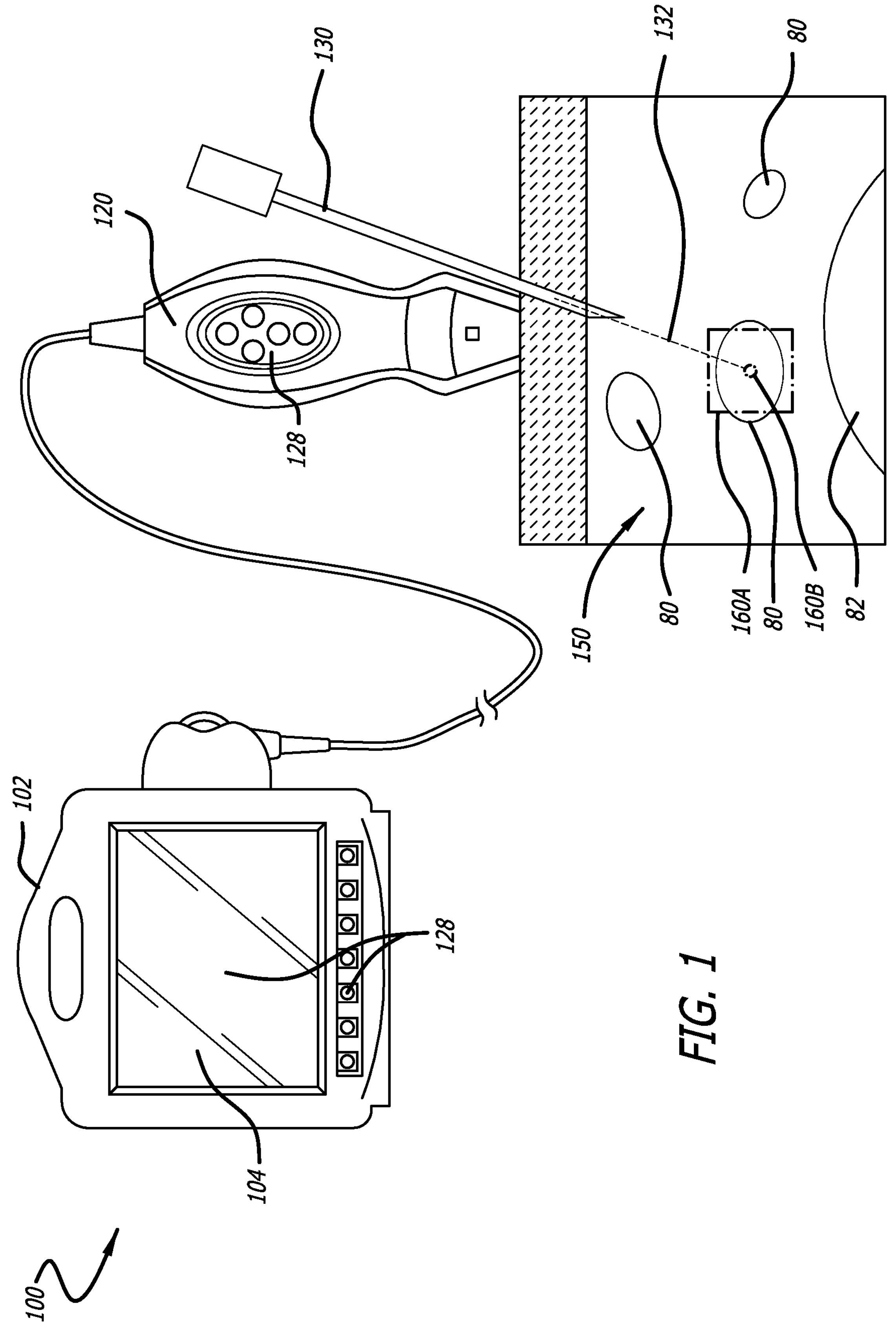
FIG. 1 shows a perspective view of a non-uniform imaging system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

FIG. 1 shows an embodiment of a non-uniform imaging system ("system") 100 that generally includes a console 102 including a display 104, and a probe 120 configured to emit and receive signals to determine an image of a subcutaneous target area 150 of a patient. In an embodiment, the probe 120 can be configured to emit and receive signals and communicate this information to the console 102 to determine the image of the target area 150. In an embodiment, the system 100 can be configured to send and receive signals of one or more modalities. Exemplary modalities can include acoustic, ultrasonic, electromagnetic, magnetic (i.e. static magnetic field, or permanent magnet), optical, electrical, ECG signals, combinations thereof, or the like.

In an embodiment, one or both of the console 102 and the probe 120 can include one or more controls 128 configured to receive an input from the user, for example to modify one or more image parameters or the like. The one or more controls 128 can include physical buttons, keyboards, sliders, or the like, or can include a user interface, touchscreen, or the like, or combinations thereof.

In an embodiment, the system 100 can include a multi-modal imaging system and can use one or more modalities to image a target area 150 and track a medical device 130 relative to the target image 150. For example, the system 100 can use an ultrasound modality to image the target area 150 and can use a magnetic and/or ECG based modalities to track and/or confirm a position of the medical device 130 relative to the probe 120. The system 100 can then provide an ultrasound image of the target area 150 and overlay one or more icons on the image of the target area 150, indicating a location and/or a trajectory 132 of the medical device 130 relative to the target area 150. Further details and embodiments of multi-modal imaging and tracking systems can be found in U.S. Pat. Nos. 8,388,541, 8,971,994, 9,492,097, 9,636,031, 10,238,418, 10,966,630, 11,027,101, US 2018/0116551, US 2018/0304043, US 2019/0069877, US 2019/0099108, US 2020/0054858, US 2020/0237255, and US 2020/0345983, each of which is incorporated by reference in its entirety into this application.

Figure 2:
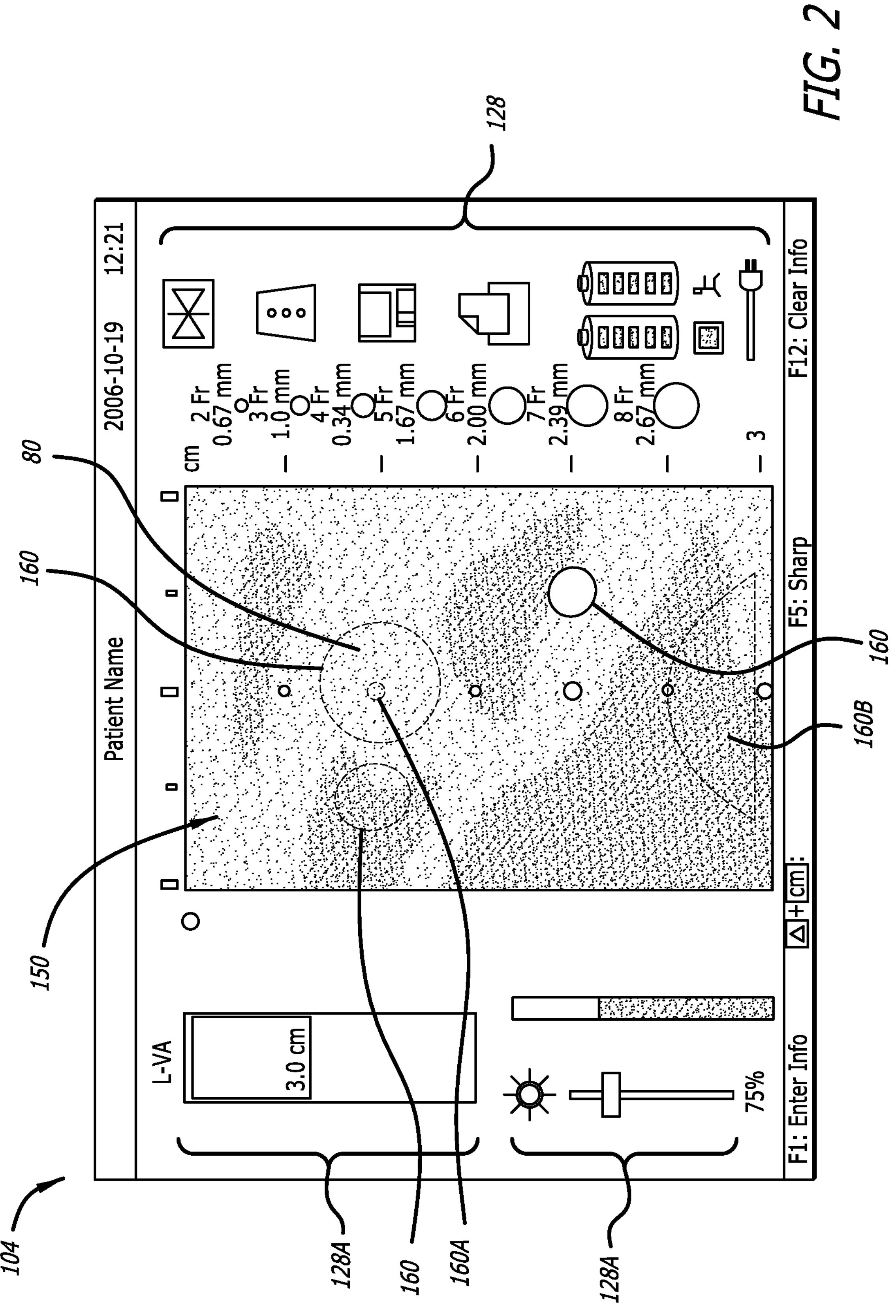
FIG. 2 shows a screenshot from a display of a non-uniform imaging system, in accordance with embodiments disclosed herein.

FIG. 2 shows an exemplary screenshot of the display 104 of the system 100 including an image of the target area 150 and one or more controls 128, as described herein. In an embodiment, the system 100 can determine one or more target locations 160 within the target area 150. The target location 160 can include a region of the target area 150 or a specific structure imaged within the target area 150 such as a target vessel, tissue, intersection point, or similar point of focus, depending on the procedure being performed. Each of these target locations 160 can be at different locations, depths, can include different tissues or structures, or are required to image different procedures performed at the target location 160. Conventional imaging techniques require the image parameters for the target area 150 as a whole to be modified to suit a specific target location 160, e.g. a first target location 160A. Exemplary image parameters can include, but not limited to, the image focus, contrast, gain, and/or other image transforms, or the like. However, these modified image parameters can be suboptimal for the rest of the target area 150, outside of the first target location 160A, or may be suboptimal for one or more second target locations 160B.

In an embodiment, a first set of controls 128A can be configured to modify one or more image parameters of the target area 150. In an embodiment, a second set of controls 128B can be configured to modify one or more image parameters of one or more target locations 160. As such, the image parameters for the target location 160 can be modified independently of the image parameters for the target area 150. In an embodiment, the image parameters for a first target location 160A can be modified independently of the image parameters for one or both of the target area 150 and a second target location 160B.

In an embodiment, an image parameter can include but not limited to the image focus, contrast, gain, and/or other image transforms. In an embodiment, the image parameter can be modified between a first value and a second value along a binary or qualitative scale, e.g. on/off, low/medium/high, or similar category or grouping. In an embodiment, the image parameter can be modified between a first value and a second value along a quantitative scale, e.g. along a slider, numerical value, or similar continuum.

In an embodiment, the system 100 can be configured to receive an input from a user to identify one or more target locations 160, for example, a first target location 160A and/or a second target location 160B. In an embodiment, the system 100 can be configured to automatically determine one or more target locations 160 within the target area 150, for example, using artificial intelligence (A.I.), machine learning techniques, neural networks, Doppler ultrasonography, combinations thereof, or the like. In an embodiment, the system 100 can be configured to receive an input from a user to confirm which of the one or more target locations 160, automatically determined by the system 100, are the selected target location(s) 160.

Figure 3B:
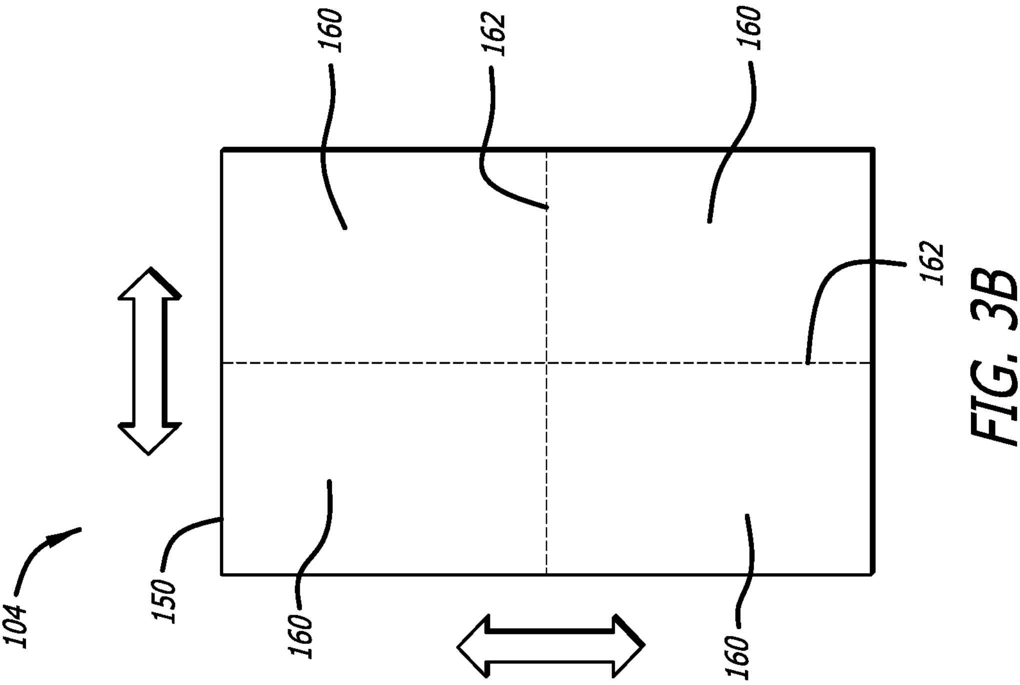
FIGS. 3A-3D show exemplary configurations of target locations within a target area for a non-uniform imaging system, in accordance with embodiments disclosed herein.
Figure 3A:
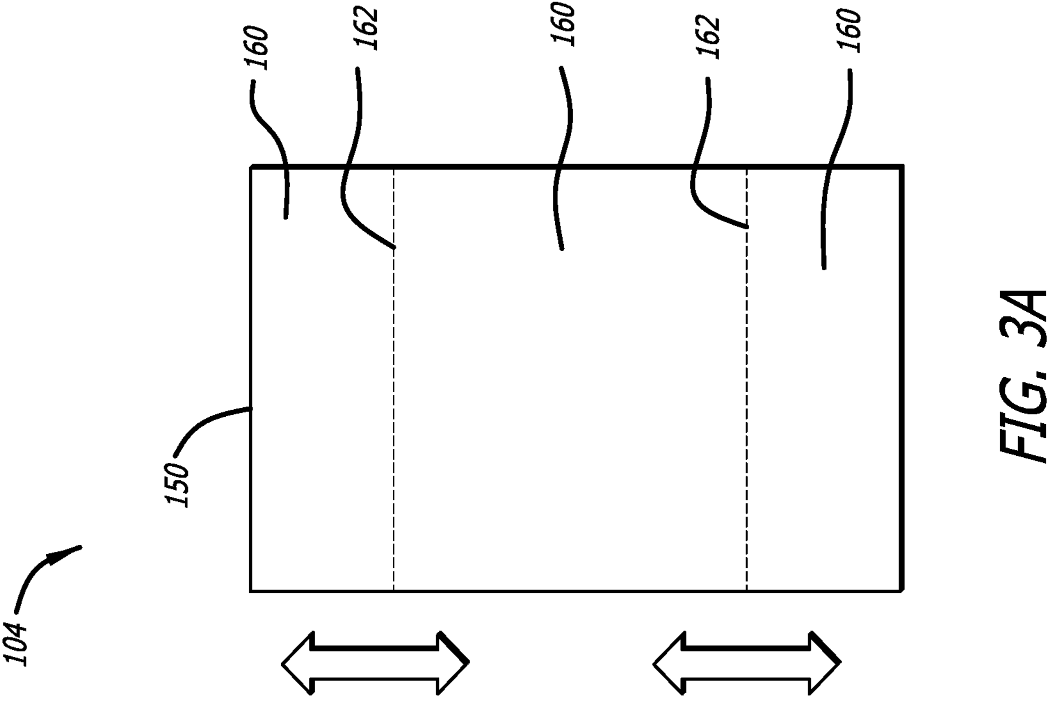

FIGS. 3A-3D show various exemplary target locations 160 within a target area 150. As shown in FIGS. 3A-3B, in an embodiment, the target location 160 can be a region of the target area 150, for example a top, middle, or bottom region, or a left or right region, or combinations thereof. In an embodiment, a perimeter 162 of the target location 160 can be modified by the user, for example, by sliding a perimeter up or down, left or right, etc.

Figure 3D:
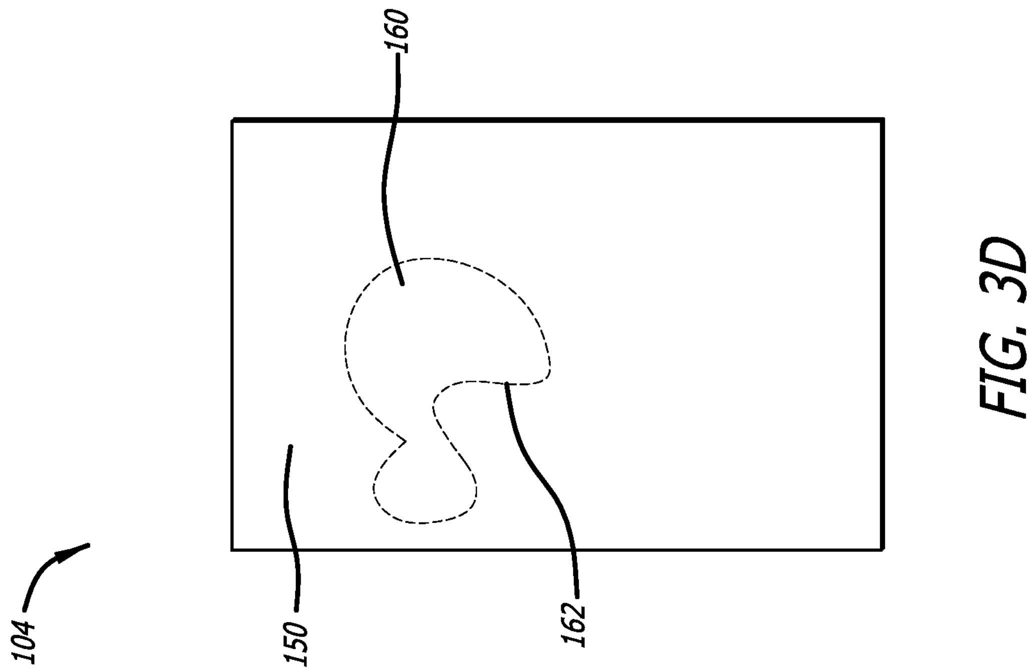
Figure 3C:
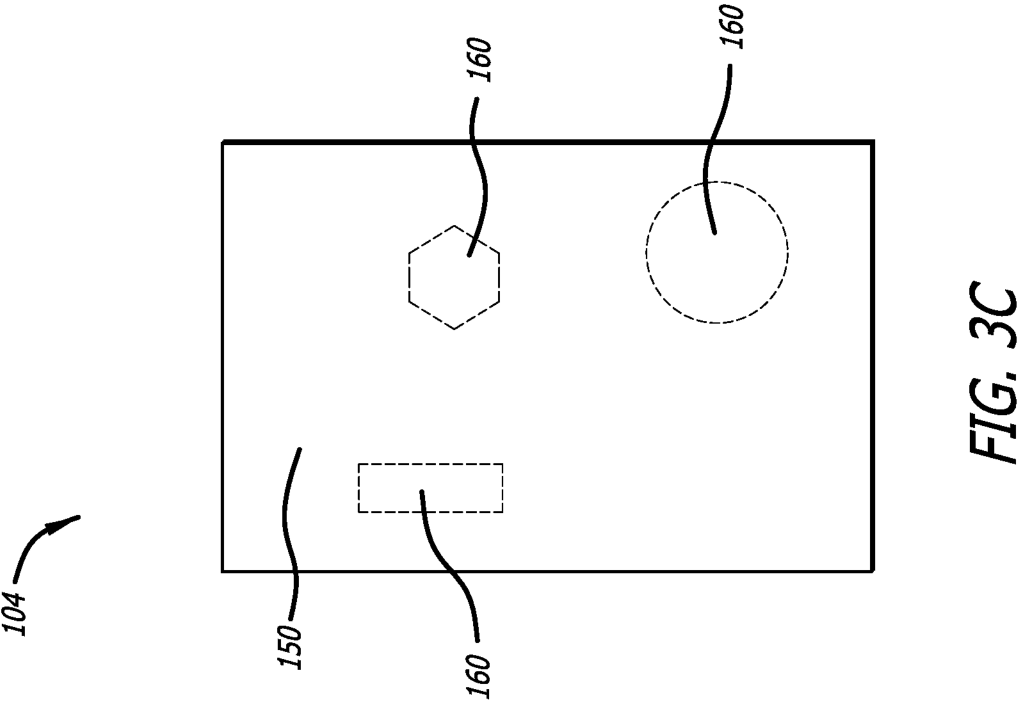

In an embodiment, as shown in FIGS. 3C-3D, the target location 160 can be identified by a point, a circle, a rectangle, or similar polygonal shape that can be repositioned and/or resized relative to the target area 150 to identify one or more target locations 160. In an embodiment, the console 102 can be configured to receive an input from the user to reposition and/or resize the target location 160 relative to the target area 150. In an embodiment, the console 102 can be configured to receive an input from the user to define a regular or irregular, polygonal shape, or "free-hand" target location 160. For example, as shown in FIG. 3D, a user can use a touchscreen control 128 to "draw" a perimeter 162 on the target area 150 and define a target location 160. In an embodiment, a first target location 160A can be within or overlap a second target location 160B and the system 100 can receive an input from a user to confirm which target location 160 takes preference over the other when modifying one or more image parameters.

Figure 4:
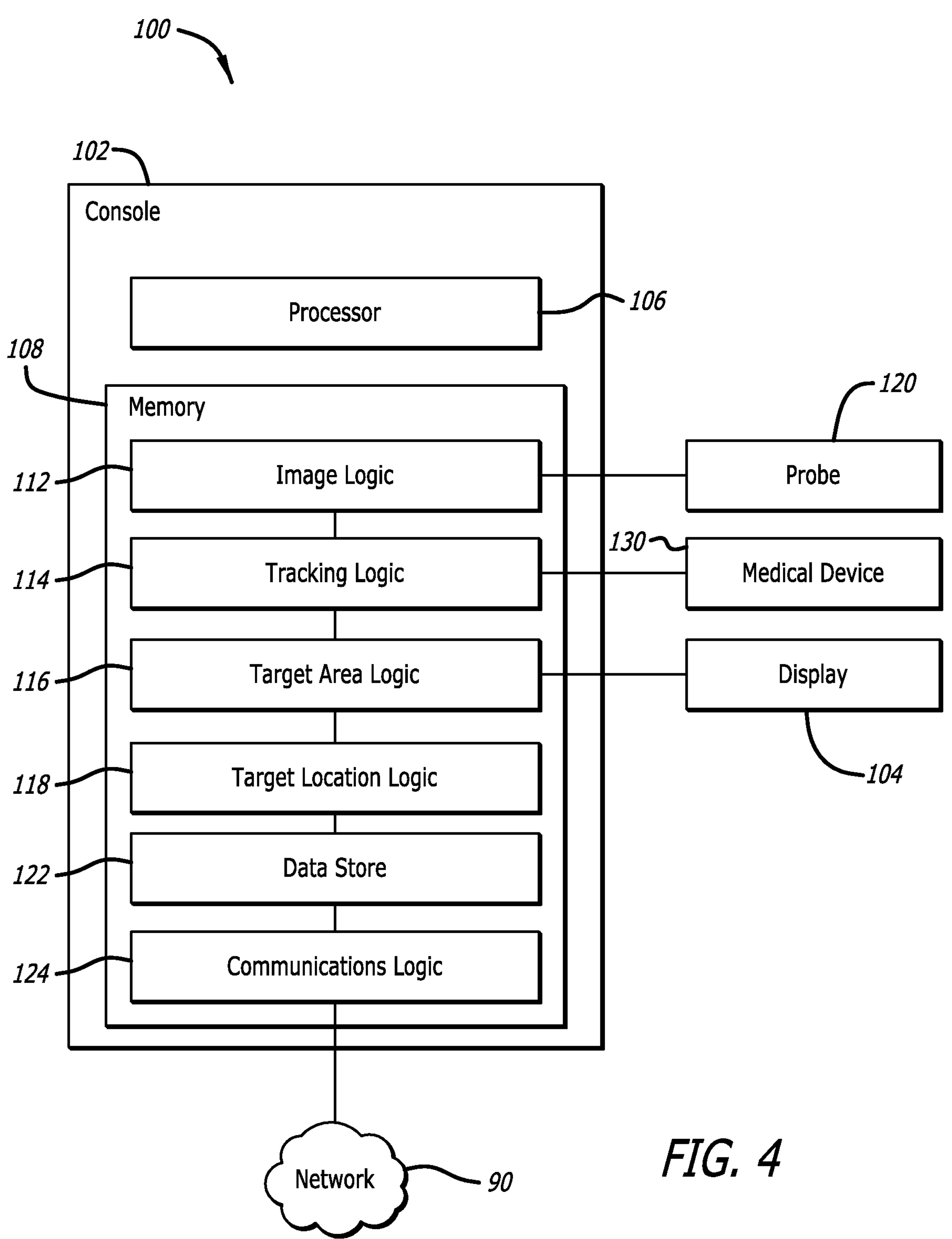
FIG. 4 shows a schematic view of a non-uniform imaging system, in accordance with embodiments disclosed herein.

FIG. 4 shows a schematic view of the system 100. In an embodiment, the console 102 includes one or more processors 106, a memory 108, a data store 122, and one or more logic engines, for example, an image logic 112, tracking logic 114, target area logic 116, target location logic 118, and a communications logic 124. It will be appreciated that the console 102 can take one of a variety of forms and may include additional components (e.g., power supplies, ports, interfaces, etc.) that are not directed to aspects of the disclosure. The one or more processors 106, with access to the memory 108 (e.g., non-volatile memory or non-transitory, computer-readable medium), are included to control functionality of the console 102 during operation.

In an embodiment, the one or more logic engines may receive and process data, as described herein. The one or more logic engines may be in the form of a software application that is loaded on the console 102 and executable by the one or more processors 106. In other embodiments, the one or more logic engines need not be loaded on the console 102 but may instead execute within a cloud computing environment (which may also be represented by the network 90) such that data from the memory 108 are communicated to the one or more logic engines for processing, for example by way of the communications logic 124. Thus, any of the one or more logic engines represented as being part of the console 102 may include an application programming interface (API) that is configured to transmit and receive data communication messages to and from the one or more logic engines operating in the cloud computing environment, i.e. network 90.

In an embodiment, the image logic 112 can be configured to send and receive signals to/from the probe 120 and determine an image of the target area 150. In an embodiment, the tracking logic 114 can be configured to send and receive signals to/from the probe 120 and determine one or more of a location, orientation, or trajectory 132 of a medical device 130. In an embodiment, the tracking logic 114 can be configured to send and receive signals to/from the medical device 130 and determine one or more of a location, orientation, or trajectory 132 of a medical device 130. This information can be communicated with the image logic 112 to overlay this information on to the image of the target area 150. In an embodiment, the target area logic 116 can be configured to collate information from one or both of the image logic 112 and the tracking logic 114 as well as one or more inputs from a user to modify an image parameter of the target area 150. In an embodiment, the target location logic 118 can be configured to determine one or more target locations 160 within the target area 150, and/or receive one or more inputs from a user to define a target location 160 within the target area 150. Further, the target location logic 118 can be configured to receive one or more inputs from a user to modify an image parameter of the target location 160.

In an embodiment, the display 104 may be a liquid crystal diode (LCD) display, or "touchscreen" display, integrated into the console 102 and employed as a user interface to display information to the user, especially during an instrument placement procedure. In an embodiment, the display 104 may be separate from the console 102. In an embodiment, a user interface is configured to provide a user with one or more controls 128 of the console 102.

In an exemplary method of use, the system 100 can image a target area 150 using the probe 120 and can display the image on the display 104 of the console 102. In an embodiment, the system 100 can image the target area 150 using an ultrasound modality. The system 100 can further detect a location of a medical device 130, e.g. a needle or the like, relative to the probe 120. In an embodiment, the system 100 can detect a location of a medical device 130 using a magnetic tracking modality. In an embodiment, the system 100 can determine a trajectory 132 of the medical device 130 based on the location and orientation relative to the probe 120 and can overlay this information on the image of the target area 150. In an embodiment, a user can modify one or more image parameters for the image of the target area 150 as a whole, i.e. this can modify the image parameters for the entire image.

In an embodiment, the user can select one or more target locations 160 within the image of the target area 150. For example, the target location can be a region of the target area, such as an upper half or lower half of the image of the target area 150, a right side or left side of the target area 150, combinations thereof, or the like. It will be appreciated however, that these regions are exemplary and non-limiting and other numbers and configurations of these regions are also contemplated. In an embodiment, the target location 160 can be a circle or similar regular or irregular polygon within the target area 150. In an embodiment, the user can modify the size, shape or position of the target location 160 within the target area 150. In an embodiment, the target location 160 can be a point within the target area 150, such as a point where the trajectory 132 of the medical device 130 intersects a vessel. In an embodiment, the user can select one or more target locations 160. In an embodiment, the system 100 can automatically identify one or more target locations 160. In an embodiment, the user can select one or more of the predetermined target locations 160 selected by the system 100.

Once the one or more target locations 160 have been determined, the system 100 can be configured to receive an input from the user to modify the image parameters of a target location 160 independently of the image parameters of the target area 150. For example, the system 100 can automatically identify one or more vessels 80 or tissue regions 82 within the target area 150 and define these as target locations 160. The system 100 can then modify the image parameters for these target locations 160 independently of the rest of the target area 150. For example, a bone tissue 82 can differ in density or depth relative to a vessel 80 and as such may require different image parameters to clearly visualize the target location 160 relative to other target locations, or areas of the target area 150 outside of the target locations 160. In an embodiment, a user can further modify the size or position of the target location 160 or the image parameter of the target location 160.

In an embodiment, a medical device 130 can be configured to access a target vessel of a first target location 160A. The system 100 can track a location and orientation of the medical device 130 relative to the probe 120 and determine a trajectory 132 of the medical device 130. Where the trajectory 132 intersects a target vessel of the first target location 160A, a second target location 160B can identify an intersection point of the medical device 130 with the target vessel, i.e. the first target location 160A. The image parameter of the second target location 160B can then be modified independently of the first target location 160A. For example, the second target location 160B image parameters can be optimized for needle or blood flash visualization without modifying the image parameters of the target vessel location 160A, and/or the target area 150 as a whole.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A subcutaneous imaging system, comprising:

a probe configured to emit an ultrasonic signal and receive a reflected ultrasonic signal; and a console communicatively coupled to the probe and including a display, the console configured to:

i) receive information from the probe and display an image of a target area disposed subcutaneously;

ii) determine a target location within the target area;

iii) modify an image parameter of the target area to a first value; and iv) modify the image parameter of the target location to a second value different from the first value while maintaining the image parameter of the target area outside of the target location at the first value.

2. The subcutaneous imaging system according to claim 1, wherein the console is further configured to determine one or both of a location and an orientation of a medical device, relative to the probe, and overlay an icon on the target area to indicate one or more of the location, the orientation, or a trajectory of the medical device relative to the target area.

3. The subcutaneous imaging system according to claim 2, wherein the medical device includes a magnetic field having a magnetic field strength, and wherein the probe is configured to detect the magnetic field strength of the medical device to determine one or both of the location and the orientation of the medical device.

4. The subcutaneous imaging system according to claim 2, wherein the medical device includes one of a needle, a stylet, a guidewire, a trocar, or a catheter.

5. The subcutaneous imaging system according to claim 1, wherein the console is further configured to determine the target location within the target area using one or more of artificial intelligence, machine learning, neural networks, or Doppler ultrasonography.

6. The subcutaneous imaging system according to claim 1, wherein the console is further configured to receive an input from a user to determine the target location within the target area.

7. The subcutaneous imaging system according to claim 1, wherein the image parameter includes one of an image focus, an image contrast, an image gain, or an image transform.

8. The subcutaneous imaging system according to claim 1, wherein one of the first value or the second value includes one of a quantitative value or a qualitative value.

9. The subcutaneous imaging system according to claim 1, wherein the target location can include one or more of a vessel, a tissue structure, a point of interception, or a region of the target area.

10. A method of imaging system a target area disposed subcutaneously, comprising:

displaying an image of the target area using a medical imaging system;

determining a target location within the target area;

modifying an image parameter of the target area to a first value; and modifying the image parameter of the target location to a second value different from the first value while maintaining the image parameter of the target area outside of the target location at the first value.

11. The method according to claim 10, wherein the medical imaging system includes an ultrasound imaging system having a console and a probe.

12. The method according to claim 11, wherein the console is further configured to receive an input from a user to determine the target location within the target area.

13. The method according to claim 10, further including displaying an icon on the image of the target area to indicate one or more of a location, an orientation, or a trajectory of a medical device relative to the target area.

14. The method according to claim 13, further including detecting a magnetic field strength of the medical device to determine one or both of the location and the orientation of the medical device.

15. The method according to claim 13, wherein the medical device includes one of a needle, a stylet, a guidewire, a trocar, or a catheter.

16. The method according to claim 10, wherein determining the target location within the target area further includes using one or more of artificial intelligence, machine learning, neural networks, or Doppler ultrasonography.

17. The method according to claim 10, wherein the image parameter includes one of an image focus, an image contrast, an image gain, and an image transform.

18. The method according to claim 10, wherein one of the first value or the second value includes one of a quantitative value or a qualitative value.

19. The method according to claim 10, wherein the target location can include one or more of a vessel, a tissue structure, a point of interception, or a region of the target area.

* * * * *